United States Patent
Hankiewicz et al.

(10) Patent No.: US 9,207,169 B2
(45) Date of Patent: Dec. 8, 2015

(54) LASER SPECTROMETER AND METHOD FOR MEASURING CONCENTRATION OF A GAS COMPONENT IN A MEASUREMENT GAS

(71) Applicant: SIEMENS AKTIENGESELLSCHAFT, Munich (DE)

(72) Inventors: Thomas Hankiewicz, Karlsruhe (DE); Piotr Strauch, Rülzheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/381,103

(22) PCT Filed: Feb. 19, 2013

(86) PCT No.: PCT/EP2013/053247
§ 371 (c)(1),
(2) Date: Aug. 26, 2014

(87) PCT Pub. No.: WO2013/127657
PCT Pub. Date: Sep. 6, 2013

(65) Prior Publication Data
US 2015/0042991 A1      Feb. 12, 2015

(30) Foreign Application Priority Data
Feb. 27, 2012    (DE) .................. 10 2012 202 893

(51) Int. Cl.
*G01N 21/27*      (2006.01)
*G01N 21/31*      (2006.01)
(Continued)

(52) U.S. Cl.
CPC . *G01N 21/31* (2013.01); *G01J 3/10* (2013.01); *G01J 3/4338* (2013.01); *G01N 21/39* (2013.01);
(Continued)

(58) Field of Classification Search
CPC .............. G01N 21/39; G01N 21/3504; G01N 2021/399; G01J 3/42; G01J 3/4338
USPC ................... 356/432–440, 300, 326; 250/573
See application file for complete search history.

(56) References Cited

U.S. PATENT DOCUMENTS 4,937,448 A      6/1990 Mantz et al.
5,742,399 A  *   4/1998 McAndrew et al. .......... 356/437
(Continued)

FOREIGN PATENT DOCUMENTS

CN      1258352      6/2000
DE      10345507     5/2005
(Continued)

*Primary Examiner* — Hoa Pham
(74) *Attorney, Agent, or Firm* — Cozen O'Connor

(57) ABSTRACT

A laser spectrometer and method for measuring gas component concentration in a measurement gas, wherein light intensity from a wavelength-tunable laser diode is detected after irradiation of the measurement gas and a reference gas, and the concentration of the gas component is determined based on reduction of the light intensity by the absorption of light at the position of a selected absorption line of the gas component, and the position of the absorption line of the gas component is referenced based on a selected absorption line of the reference gas, and wherein there is a mixed operation consisting of actual measurements of fast concentration changes of the gas component to be measured and a short reference/standardization phase for wavelength referencing, line locking and standardization, where the duration of the actual measurement is measured such that measuring conditions remain constant and do not deviate from those during the reference/standardization phase.

5 Claims, 3 Drawing Sheets

(51) Int. Cl.
  *G01N 21/39* (2006.01)
  *G01J 3/10* (2006.01)
  *G01J 3/433* (2006.01)
  *G01N 33/00* (2006.01)
  *G01N 21/3504* (2014.01)

(52) U.S. Cl.
  CPC ........ *G01N 33/0027* (2013.01); *G01N 21/3504* (2013.01); *G01N 2021/399* (2013.01); *G01N 2201/0691* (2013.01)

(56) References Cited

U.S. PATENT DOCUMENTS

| | | | |
|---|---|---|---|
| 6,351,309 B1 * | 2/2002 | Bomse et al. | 356/437 |
| 6,519,039 B1 | 2/2003 | Morishita et al. | |
| 2005/0046852 A1 | 3/2005 | Larking et al. | |
| 2005/0140979 A1 | 6/2005 | Kluczynski et al. | |
| 2006/0044562 A1 * | 3/2006 | Hagene et al. | 356/437 |
| 2007/0131882 A1 * | 6/2007 | Richman | 250/573 |
| 2007/0229834 A1 * | 10/2007 | Patel et al. | 356/432 |
| 2008/0304066 A1 | 12/2008 | Kluczynski et al. | |
| 2009/0086206 A1 * | 4/2009 | Mori | 356/326 |
| 2009/0201507 A1 | 8/2009 | Kluczynski et al. | |
| 2010/0201989 A1 * | 8/2010 | Zhou et al. | 356/437 |
| 2014/0247843 A1 * | 9/2014 | Steinbacher | 372/20 |
| 2014/0253922 A1 * | 9/2014 | Liu et al. | 356/437 |
| 2015/0014541 A1 * | 1/2015 | Depenheuer et al. | 250/341.1 |
| 2015/0085288 A1 * | 3/2015 | Steinbacher | 356/437 |

FOREIGN PATENT DOCUMENTS

| | | |
|---|---|---|
| EP | 1510798 | 3/2005 |
| EP | 2000792 | 12/2008 |
| EP | 2072979 | 6/2009 |
| GB | 2153994 A | 8/1985 |

* cited by examiner

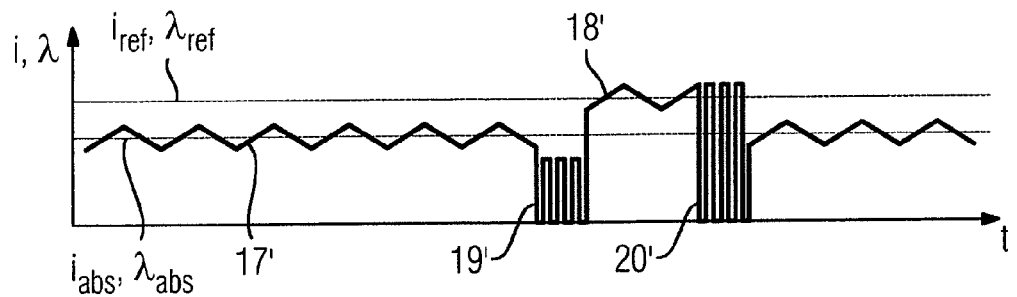
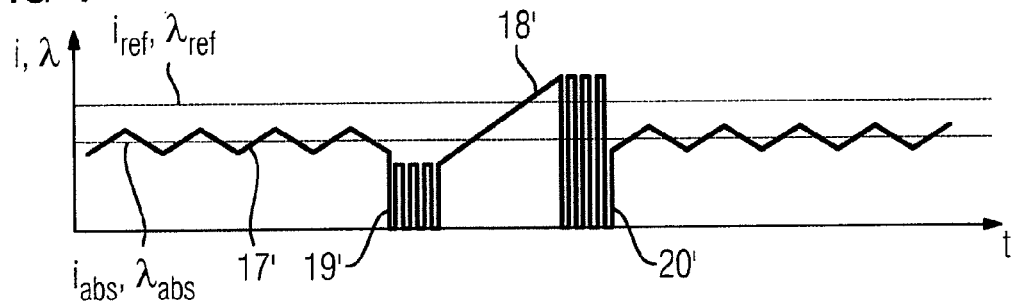
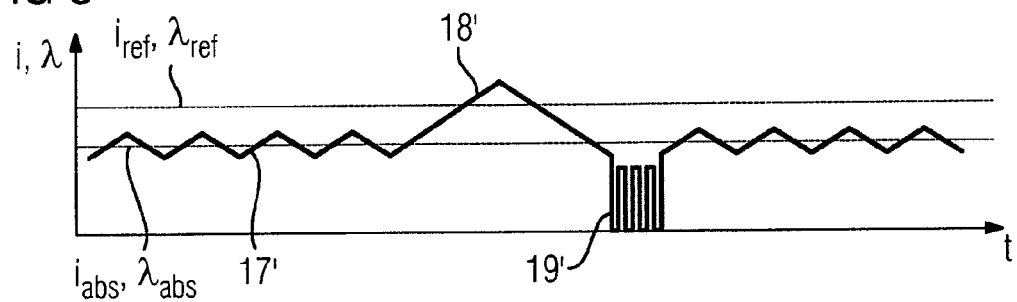
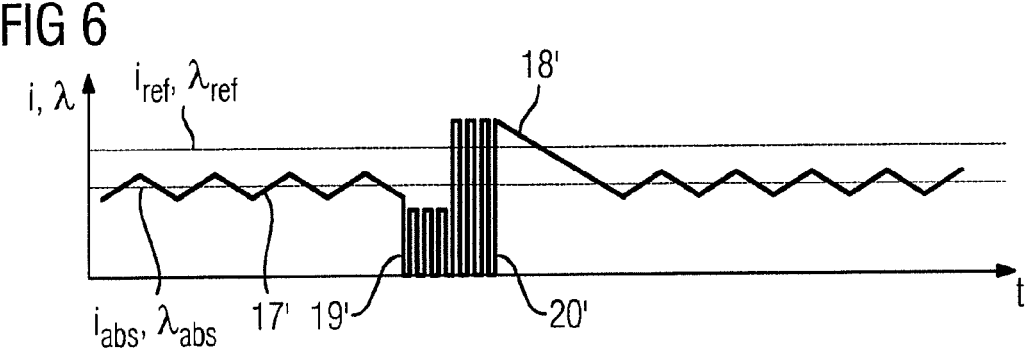

LASER SPECTROMETER AND METHOD FOR MEASURING CONCENTRATION OF A GAS COMPONENT IN A MEASUREMENT GAS

REFERENCE TO RELATED APPLICATIONS

This is a U.S. national stage of application No. PCT/EP2013/053247 filed 19 Feb. 2013. Priority is claimed on German Application No. 10 2012 202 893.5 filed 27 Feb. 2012, the content of which is incorporated herein by reference in its entirety.

BACKGROUND OF THE INVENTION

1. Field of the Invention

The invention relates to laser spectrometers and, more particularly, to a laser spectrometer and method for measuring the concentration of a gas component in a measurement gas.

2. Description of the Related Art

Laser spectrometers are particularly used for optical gas analysis in process measurement technology. Here, a laser diode generates light in the infrared range, which is guided through the process gas to be measured (the measurement gas) and is subsequently detected. The wavelength of the light is tuned to a specific absorption line of the gas component respectively to be measured, the laser diode periodically sampling the absorption line. To this end, the laser diode is driven periodically with a ramp-shaped or triangular (increasing and decreasing ramp) current signal. The concentration of the gas component of interest can be determined from the absorption detected at the position of the absorption line.

The intensity and wavelength of the light generated are nonlinear functions of the injection current and of the operating temperature of the laser diode. As a result, wavelength referencing is necessary in many cases. To this end, a reference gas is additionally introduced in a known concentration into the light path, and an absorption line of the reference gas is measured. The temperature of the laser diode can then be regulated via the position of the absorption line of the reference gas, such that the absorption line of the gas compared to be measured always lies at a particular position of the ramp of the current signal. In this case, the current ramp must be large enough for the laser diode sampling range resulting therefrom to cover both the absorption line of the gas component to be measured and that of the reference gas.

When shining through the measurement gas and reference gas, besides the wavelength-dependent absorption by infrared-active gas components, wavelength-independent absorption also takes place by optical components (e.g., windows) or aerosols (e.g., smoke particles). This makes normalization of the measurement necessary. To this end, the laser diode can be driven regularly with at least one burst current signal, the amplitude of which lies outside the value range of the ramp-shaped or triangular current signal, so that the light wavelengths generated with the burst current signal lie outside the wavelength ranges of the absorption lines of the gas components to be measured and other infrared-active gas components. This makes it possible to normalize the light intensity detected at the position of the absorption line to be measured, by division by the light intensity detected at the position of the burst current signal (EP 2 072 979 A1).

As explained above, in contemporary laser spectrometers a wavelength range that covers both the absorption lines of the gas components to be measured and the absorption lines for the wavelength referencing is sampled. In addition, a time window is required for the normalization of the measurement. Each sampling period therefore claims much more time than is necessary for the detection of a single absorption line. The time resolution of the measurement, in the case of rapidly varying gas concentrations, is thereby limited.

SUMMARY OF THE INVENTION

It is therefore an object of the invention to increase the measurement speed in the laser-spectrometric determination of the concentration of a gas component in a measurement gas.

This and other objects and advantages are achieved by the method and the laser spectrometer in accordance with the invention by providing a method for measuring the concentration of a gas component in a measurement gas, by detecting the intensity of the light of a wavelength-tunable laser diode after shining through the measurement gas and a reference gas and determining the concentration of the gas component with the aid of the reduction in the light intensity due to the absorption of the light at the position of a selected absorption line of the gas component, the position of the absorption line of the gas component being referenced with the aid of a selected absorption line of the reference gas. In accordance with the method of the invention, the laser diode is driven periodically with a first increasing and/or decreasing current signal to sample the absorption line of the gas component wavelength-dependently in a sampling range which lies outside the absorption line of the reference gas and which is restricted to the immediate vicinity of the absorption line of the gas component. Next, the laser diode is driven regularly with a second increasing and/or decreasing current signal to sample the absorption line of the reference gas wavelength-dependently in a sampling range which either contains the two absorption lines of the gas component and of the reference gas or lies outside the absorption line of the gas component and is restricted to the immediate vicinity of the absorption line of the reference gas. The laser diode is then driven regularly with at least one burst current signal having an amplitude lying outside the value ranges of the first and second current signals to normalize the light intensity detected at the position of the absorption line with the intensity detected at the position of the at least one burst current signal. Finally the first current signal, the second current signal and the burst current signal are generated successively such that individual or a few, generated directly after one another, second current signals and burst current signals alternate with a multiplicity of first current signals generated directly after one another.

It is also an object of the invention to provide a laser spectrometer for measuring the concentration of a gas component in a measurement gas, where the laser spectrometer includes a wavelength-tunable laser diode, the light of which, after shining through the measurement gas and a reference gas, strikes a detector having a downstream evaluation device in which the concentration of the gas component is determined with the aid of the reduction in the light intensity due to the absorption of the light at the position of a selected absorption line of the gas component, the position of the absorption line of the gas component being referenced with the aid of an absorption line of the reference gas.

The spectrometer also includes a first signal generator for periodic driving of the laser diode with a first increasing and/or decreasing current signal to sample the absorption line of the gas component wavelength-dependently in a sampling range that lies outside the absorption line of the reference gas and which is restricted to the immediate vicinity of the absorption line of the gas component, a second signal generator for regular driving of the laser diode with a second increasing and/or decreasing current signal to sample the absorption line of the reference gas wavelength-dependently in a sampling range which either contains the two absorption lines of the gas component and of the reference gas or lies outside the absorption line of the gas component and is restricted to the immediate vicinity of the absorption line of the reference gas, at least one third signal generator for regular driving of the laser diode with at least one burst current signal having an amplitude lying outside the value ranges of the first and second current signals to normalize the light intensity detected at the position of the absorption line with the intensity detected at the position of the at least one burst current signal, and a time generator which controls the signal generators such that the first current signal, the second current signal and the burst current signal are generated successively, with individual or a few, generated directly after one another, second current signals and burst current signals alternating with a multiplicity of first current signals generated directly after one another.

With the method in accordance with the invention, or in the laser spectrometer in accordance with the invention, mixed operation occurs, consisting of the actual measurement (periodic microscan) of rapid concentration changes of the gas component to be measured and a short reference/normalization phase for the wavelength referencing, the line locking and the normalization. The duration of the continuous measurement must be dimensioned such that the measurement conditions remain constant and do not deviate from those during the reference/normalization phase. This applies above all to the transmission conditions, as well as the temperature and pressure.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained below with reference to the figures of the drawing with the aid of exemplary embodiments, in which:

FIGS. 2 to 6 show various examples of driving the laser diode; and

DETAILED DESCRIPTION OF THE PREFERRED EMBODIMENTS

Figure 1:
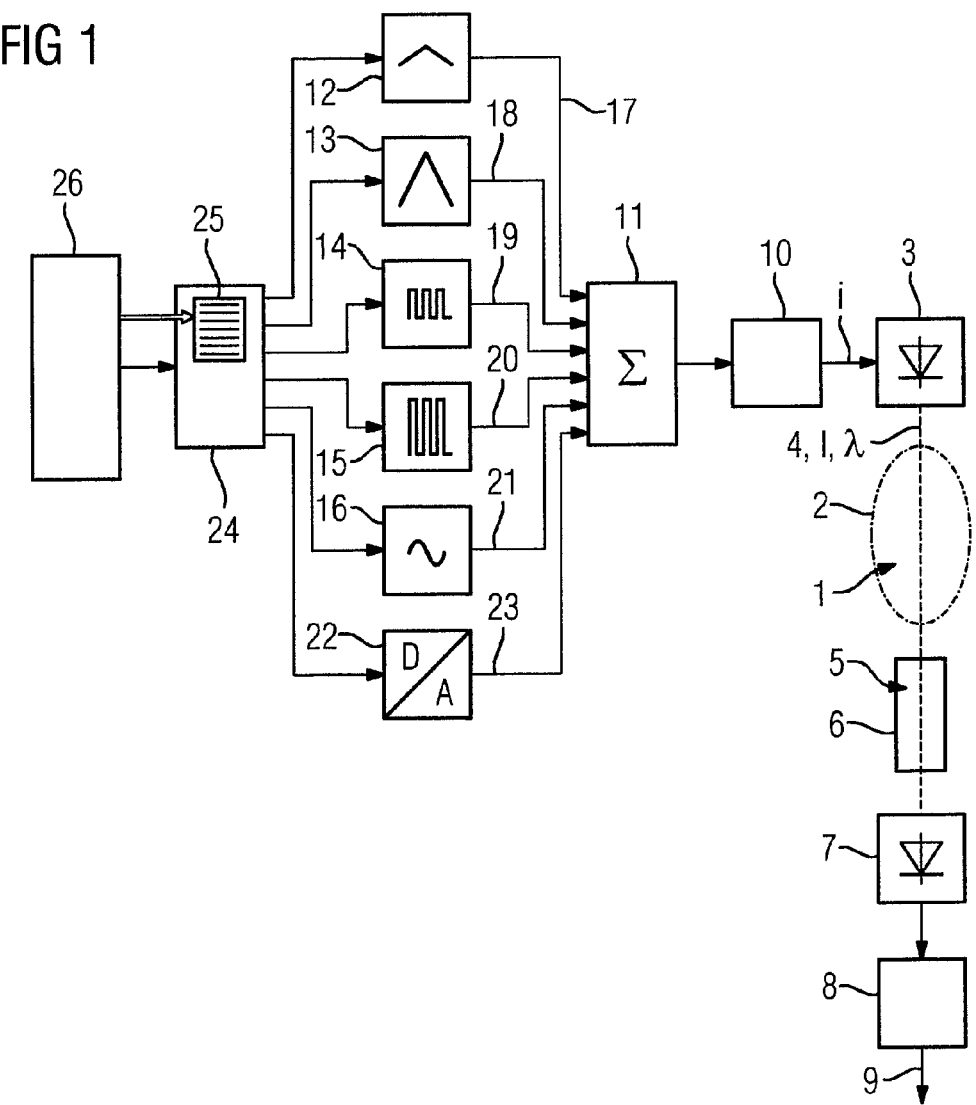
FIG. 1 shows a schematic representation of an exemplary spectrometer in accordance with the invention having a laser diode.

FIG. 1 shows a laser spectrometer for measuring the concentration of at least one gas component of interest of a measurement gas 1, which is contained in a measurement volume 2, such as a measurement cuvette or a process gas line. The spectrometer contains a laser diode 3, the light 4 of which strikes, through the measurement gas 1 and a downstream reference gas cuvette 6 filled with a reference gas 5, a detector 7 with a downstream evaluation device 8 for delivering the measurement result 9. The laser diode 3 is driven by a controllable current source 10 with an injection current i, the intensity I and the wavelength $\lambda$ of the light 4 generated depending on the current i and the operating temperature of the laser diode 3. The injection current i is generated in the form of different current signals. To this end, the current source 10 is driven via an adder 11 by different signal generators 12, 13, 14, 15, 16, of which a first signal generator 12 generates a first ramp-shaped or triangular signal 17, a second signal generator 13 generates a second ramp-shaped or triangular signal 18, a third signal generator 14 generates a first burst signal 19, a fourth signal generator 15 generates a second burst signal 20, and a fifth signal generator 16 generates a sine signal 21. A digital/analog converter 22 generates a bias signal 23, with the aid of which the current source 10 generates a bias current for the laser diode 3. The signal generators 12, 13, 14, 15, 16 are controlled by a time generator 24 in accordance with a table 25, in which it is established which of the signal generators 12, 13, 14, 15, 16 generates the relevant signal 17, 18, 19, 20 or 21 when and how often directly in succession, i.e. with which number of periods. The generation of the ramp-shaped or triangular signals 17, 18 and the burst signals 19, 20 is carried out alternately, i.e., not simultaneously, while the sine signal 21 can only be generated together with the respective ramp-shaped or triangular signals 17, 18. The table 25 is programmable and, as shown, may be implemented in the time generator 24 or, for example, in a superordinate control device 26 of the laser spectrometer.

The driving of the laser diode may be performed in different ways in the scope of the invention. For example, the adder 11 may be replaced with a switching device (multiplexer), controlled by the time generator 24, which converts the signals 17, 18, 19, 20 into a signal sequence in accordance with the table 25, and thereby drives the current source 10. The signals 17, 18 may also have other increasing and/or decreasing signal profiles, such as a sine profile.

Figure 2:
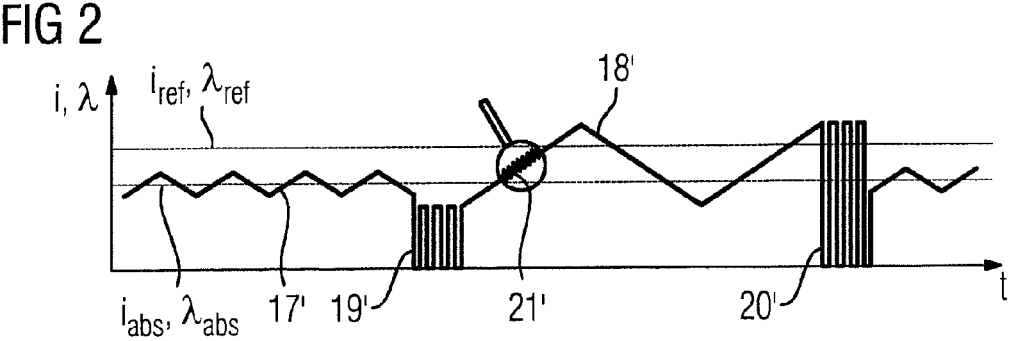

FIG. 2 shows a first example of the driving of the laser diode with the injection current i. In its time profile, the injection current i consists of different current signals 17', 18', 19', 20', 21', which result from the driving of the current source 10 with the signals 17, 18, 19, 20, 21. The wavelength $\lambda$ of the light 4 generated follows the profile of the current i more or less linearly. The absorption line of the gas component to be measured lies at the position $i_{abs}$, or $\lambda_{abs}$, and that of the reference gas at the position $i_{ref}$ or $\lambda_{ref}$.

With the first ramp-shaped or triangular current signal 17', the absorption line of the gas component is sampled in a sampling range that lies outside the absorption line of the reference gas 5 and is restricted to the immediate vicinity of the absorption line of the gas component. The sampling is performed over a prolonged time, such as one minute, with a multiplicity of sampling periods following one another directly. Owing to the relatively low amplitude of the current signal 17', the period duration is correspondingly short, so that the measurement of the absorption line of the gas component can even follow rapid concentration changes of the gas component to be measured.

The sampling of the absorption line of the gas component is interrupted regularly, here for example at minute intervals, by a measurement of the absorption line of the reference gas 5. To this end, the laser diode 3 is driven with the second ramp-shaped or triangular current signal 18', the amplitude of which, in the example shown in FIG. 2, is large enough for the resulting sampling range to contain the two absorption lines of the gas component and the reference gas 5. This second current signal 18' is generated only for a short duration in the second range or less, for a single period or very few periods.

Before and/or after the second current signal 18', the burst signals 19' and 20', respectively, used for the normalization of the measurement are generated.

In order to increase the measurement accuracy, the ramp-shaped or triangular current signals 17' and 18' may be modulated in a known way with the sine current signal 21' with the frequency f. Owing to the nonlinearity of the absorption lines, the modulation of the injection current i with the frequency f results in a corresponding variation of the detected light intensity I with more less pronounced harmonic distortions. At the extreme position (absorption maximum) in the middle of the absorption line, the first harmonic with the frequency $2f$ dominates, while the proportion of the first harmonic in the intensity I decreases greatly in wavelength ranges outside the absorption maximum. The absorption occurring at the position of the absorption maximum can therefore be determined very accurately and free from interference in the evaluation device 8 by evaluating the $2f$ signal component.

FIGS. 3 to 6 show other exemplary embodiments of the driving of the laser diode 3, in which the second current signal 18' and/or the burst current signals 19', 20', or only one burst current signal, are generated in a different sequence. The second current signal 18' may also be generated in the shape of a ramp (FIGS. 4 and 6) instead of triangularly and/or with a small amplitude, restricting the sampling to the immediate vicinity of the absorption line of the reference gas 5 (FIG. 3), in order to keep the interruption of the rapid periodic sampling of the absorption line of the gas component of interest as short as possible. A ramp-shaped signal form is naturally also possible for the first current signal 17'.

Figure 7:
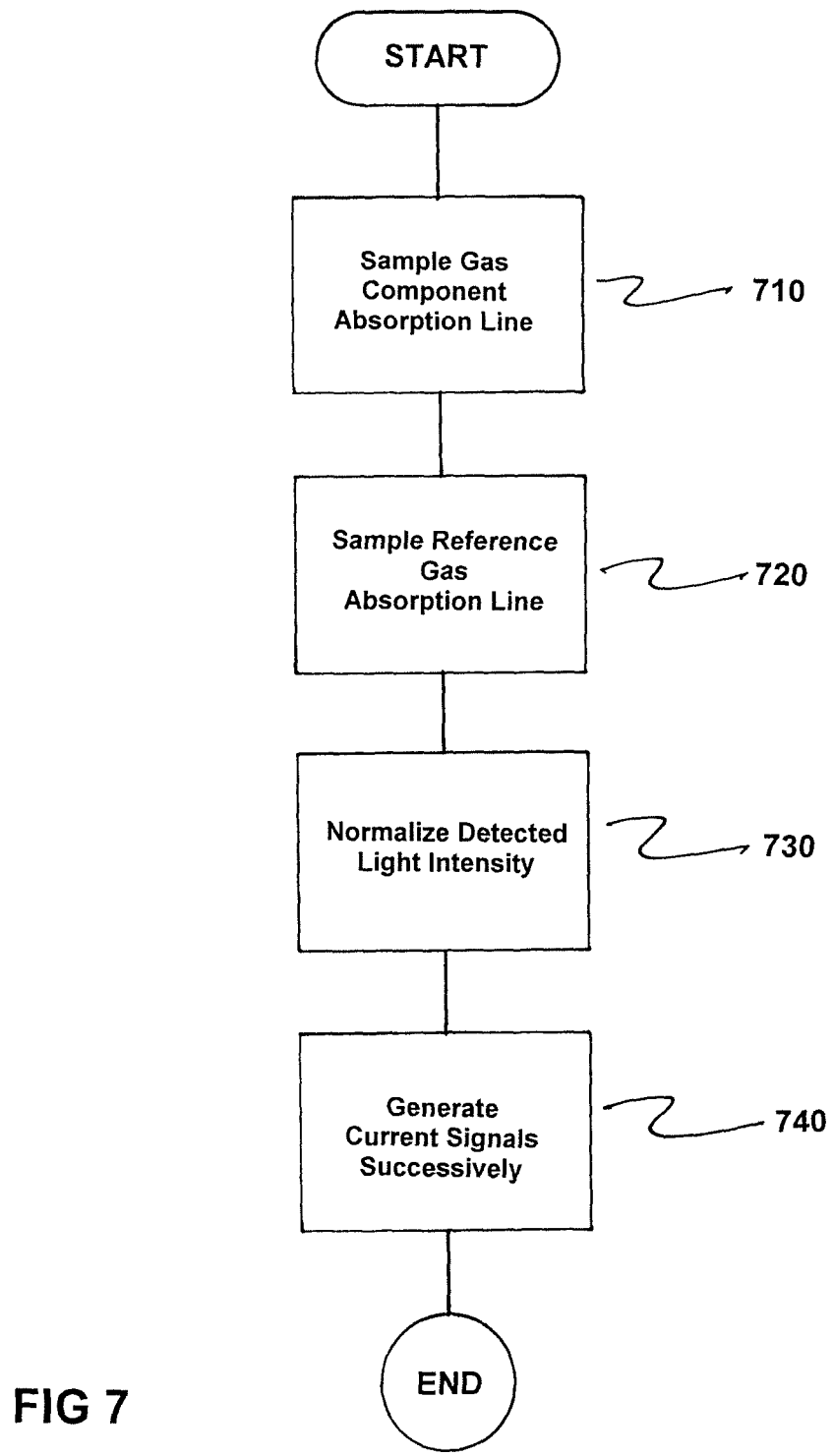
FIG. 7 is a flowchart of the method in accordance with the invention.

FIG. 7 is a flowchart of a method for measuring a concentration of a gas component in a measurement gas (1), by detecting an intensity (I) of light (4) of a wavelength-tunable laser diode (3) after shining the light through the measurement gas (1) and a reference gas (5), and by determining the concentration of the gas component aided by a reduction in the intensity (I) of the light due to absorption of the light (4) at a position (iabs, λabs) of a selected absorption line of the gas component, the position (iabs, λabs) of the absorption line of the gas component being referenced with aided by a selected absorption line of the reference gas (5). The method comprises driving the laser diode (3) periodically with at least one of (i) a first increasing current signal (17') and (ii) a first decreasing current signal (17') to sample the absorption line of the gas component wavelength-dependently in a sampling range which reside outside the absorption line of the reference gas (5) and which is restricted to an immediate vicinity of the absorption line of the gas component, as indicated in step 710.

The laser diode (3) is then driven regularly with at least one of a second increasing current signal (18') and (ii) a second decreasing current signal (18') to sample an absorption line of the reference gas (5) wavelength-dependently in a sampling range which one of (i) contains two absorption lines of the gas component and the reference gas (5) and (ii) lies outside the absorption line of the gas component and which is restricted to the immediate vicinity of the absorption line of the reference gas (5), as indicated in step 720.

Next, the laser diode (3) is driven regularly with at least one burst current signal (19', 20') having an amplitude lying outside the value ranges of the first and second current signals (17', 18') to normalize the light intensity (I) detected at the position (iabs, λabs) of the absorption line with the intensity (I) detected at the position of the at least one burst current signal (19', 20'), as indicated in step 730.

The first current signal (17'), the second current signal (18') and the at least one burst current signal (19', 20') are generated successively such that individual or a few, generated directly after one another, second current signals (18') and the at least one burst current signal (19', 20') alternate with a multiplicity of first current signals (17') generated directly after one another as indicated in step 740.

The method according to the invention is suitable for spectrometers in all bands (UV, VIS, IR).

While there have been shown, described, and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for measuring a concentration of a gas component in a measurement gas, by detecting an intensity of light of a wavelength-tunable laser diode after shining through the measurement gas and a reference gas, and by determining the concentration of the gas component aided by a reduction in the intensity of the light due to absorption of the light at a position of a selected absorption line of the gas component, the position of the absorption line of the gas component being referenced with aided by a selected absorption line of the reference gas, the method comprising:

driving the laser diode periodically with at least one of (i) a first increasing current signal and (ii) a first decreasing current signal to sample the absorption line of the gas component wavelength-dependently in a sampling range which reside outside the absorption line of the reference gas and which is restricted to an immediate vicinity of the absorption line of the gas component;

driving the laser diode regularly with at least one of a second increasing current signal and (ii) a second decreasing current signal to sample an absorption line of the reference gas wavelength-dependently in a sampling range which one of (i) contains two absorption lines of the gas component and the reference gas and (ii) lies outside the absorption line of the gas component and which is restricted to the immediate vicinity of the absorption line of the reference gas;

driving the laser diode regularly with at least one burst current signal having an amplitude lying outside the value ranges of the first and second current signals to normalize the light intensity detected at the position of the absorption line with the intensity detected at the position of the at least one burst current signal; and generating the first current signal, the second current signal and the at least one burst current signal successively such that individual or a few, generated directly after one another, second current signals and the at least one burst current signal alternate with a multiplicity of first current signals generated directly after one another.

2. The method as claimed in claim 1, wherein the generation of the first current signal, the second current signal and the burst current signal is controlled by a time generator in accordance with a table in which a number and sequence of the first and second current signals and the at least one burst current signal to be generated are stored.

3. A laser spectrometer for measuring a concentration of a gas component in a measurement gas, comprising:
- a wavelength-tunable laser diode, a light of which, after shining through the measurement gas and a reference gas, strikes a detector having a downstream evaluation device in which the concentration of the gas component is determined aided by a reduction in a light intensity due to absorption of the light at a position of a selected absorption line of the gas component, the position of the absorption line of the gas component being referenced aided by an absorption line of the reference gas;
- a first signal generator for periodic driving of the laser diode with at least one of (i) a first increasing current signal and (ii) a first decreasing current signal to sample the absorption line of the gas component wavelength-dependently in a sampling range which lies outside the absorption line of the reference gas and which is restricted to an immediate vicinity of the absorption line of the gas component;
- a second signal generator for regular driving of the laser diode with at least one of (i) a second increasing current signal and (ii) a decreasing current signal to sample the absorption line of the reference gas wavelength-dependently in a sampling range which one of contains the two absorption lines of the gas component and the reference gas and (ii) lies outside the absorption line of the gas component and which is restricted to an immediate vicinity of the absorption line of the reference gas;
- at least one third signal generator for regular driving of the laser diode with at least one burst current signal having an amplitude lying outside value ranges of the first and second current signals to normalize the light intensity detected at the position of the absorption line with the intensity detected at the position of the at least one burst current signal; and
- a time generator which controls the signal first, second and third generators such that the first current signal, the second current signal and the at least one burst current signal are generated successively, with individual or a few, generated directly after one another, second current signals and burst current signals alternating with a multiplicity of first current signals generated directly after one another.

4. The laser spectrometer as claimed in claim 3, wherein the time generator has access to a table in which a number and sequence of the first and second current signals to be generated and burst current signals are stored.

5. The laser spectrometer as claimed in claim 4, wherein the table is programmable.

* * * * *